(12) United States Patent
Deng

(10) Patent No.: US 7,954,697 B2
(45) Date of Patent: Jun. 7, 2011

(54) TAMPERPROOF GENUINENESS ID DEVICE WITH SELF-DESTRUCT PROTECTION FUNCTION AND A METHOD THEREOF

(76) Inventor: Pingxiao Deng, Shenzhen (CN)

( * ) Notice: Subject to any disclaimer, the term of this patent is extended or adjusted under 35 U.S.C. 154(b) by 0 days.

(21) Appl. No.: 12/532,169

(22) PCT Filed: Mar. 20, 2008

(86) PCT No.: PCT/CN2008/070547
§ 371 (c)(1), (2), (4) Date: Sep. 20, 2009

(87) PCT Pub. No.: WO2008/116415
PCT Pub. Date: Oct. 2, 2008

(65) Prior Publication Data
US 2010/0032478 A1    Feb. 11, 2010

(30) Foreign Application Priority Data

Mar. 26, 2007 (CN) .......................... 2007 1 0073704
Mar. 18, 2008 (CN) .......................... 2008 1 0084691

(51) Int. Cl.
G06K 17/00 (2006.01)
G06K 7/00 (2006.01)

(52) U.S. Cl. .................................. 235/375; 235/435

(58) Field of Classification Search .................. 235/375, 235/379, 380, 435, 439, 449, 451, 487, 492; 340/10, 572

See application file for complete search history.

(56) References Cited

U.S. PATENT DOCUMENTS

2005/0001040 A1* 1/2005 Berstis .......................... 235/492
2006/0273903 A1* 12/2006 Kim et al. .................. 340/572.1
2007/0182571 A1* 8/2007 Kennish et al. ............ 340/573.1
2007/0210173 A1* 9/2007 Nagel ............................ 235/492

* cited by examiner

Primary Examiner — Michael G Lee
Assistant Examiner — Matthew Mikels

(57) ABSTRACT

A tamperproof genuineness ID device with self-destruct protection function and a method thereof, which identifies whether merchandises are genuine or fake by reading, identifying and encrypting genuineness ID information in a genuineness ID medium. The tamperproof genuineness ID device includes a working part with self-destruct protection function and a detecting work part for identifying a product to be detected, wherein the product to be detected is airtight sealed or fixed with the tamperproof genuineness ID device together. The method includes several steps: setting the genuineness ID medium in a coordinate working state with the tamperproof genuineness ID device; identifying information in the genuineness ID medium by the detecting work part of the tamperproof genuineness ID device, then encrypting and calculating to obtain a native genuineness ID code; and outputting a detecting result. The tamperproof genuineness ID device makes genuineness ID detection for merchandise easier and more reliable.

11 Claims, 3 Drawing Sheets

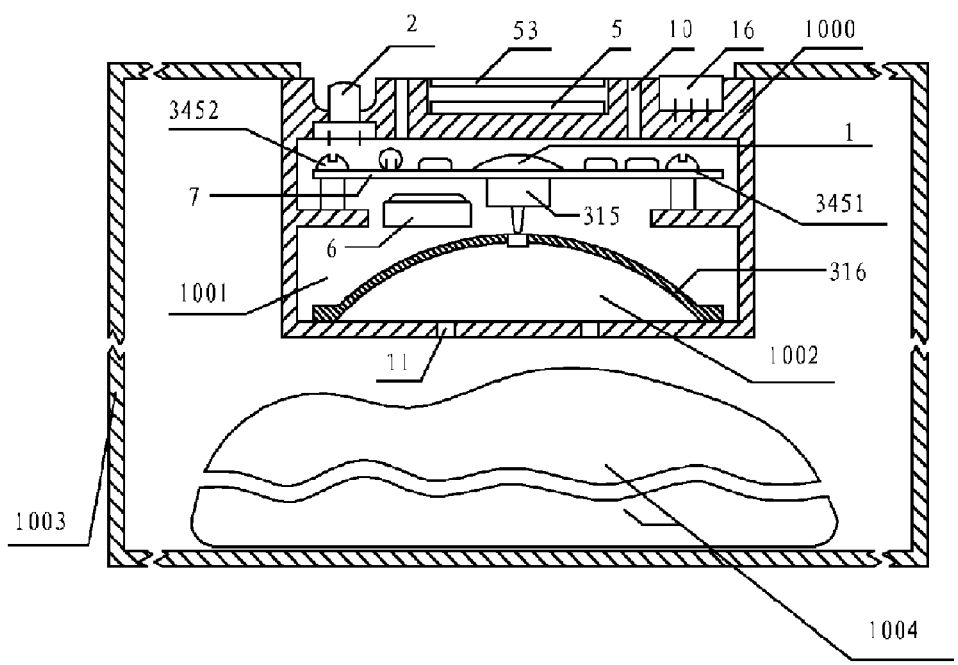

TAMPERPROOF GENUINENESS ID DEVICE WITH SELF-DESTRUCT PROTECTION FUNCTION AND A METHOD THEREOF

FIELD OF THE PATENT APPLICATION

The present invention generally relates to tamperproof genuineness ID technique for merchandise and logistics, more particularly to a tamperproof genuineness ID device with self-destruct protection function and a method thereof, which identifies whether a merchandise is genuine or fake by reading, identifying and encrypting genuineness ID information in a genuineness ID medium.

BACKGROUND

Conventional anti-counterfeiting technique for merchandise usually adopts an anti-counterfeiting outer packaging made of special material and special structure, and sets an anti-counterfeiting mark of special material and special technology on the merchandise or the outer packaging thereof, so as to distinguish the genuine from the fake by visual inspection. However, with the progress of manufacture and printing technology, counterfeiters can fake the same easily and even to mix the spurious with the genuine. Therefore, such anti-counterfeiting means can not provide anti-counterfeiting protection, and on the contrary, may provide "legal" protection for fake products.

Anti-counterfeiting codes are often used currently, however, once the Anti-counterfeiting inquiry codes on the merchandise are copied by counterfeiters, the first inquired product is considered as "real", while the subsequent inquired product is considered as "fake". The inquiry result only relates to the inquiry sequence, and without necessary relationship with the fact that the merchandise genuine or fake.

Radio Frequency Identification (RFID) anti-counterfeiting technique is a non-contact anti-counterfeiting technique with Radio Frequency used recently, in which an information card with information of the merchandise to be identified stored thereon is attached to the anti-counterfeiting merchandise, and a special reader will read the information in the card in order to distinguish the genuine from the fake. However, the RFID technology still can't change the existing passive situation of the anti-counterfeiting technique for many reasons, such as, the information stored in the card may be copied, the card peeled off from the true product may be used repeatedly, the arrangement of the reader is limited and the cost is relatively high.

SUMMARY

Accordingly, to overcome the shortcomings of current anti-counterfeiting devices that it is not unique for the true product, easy to be copied and faked, or may be displaced on the fake merchandise for reuse, which will result that the anti-counterfeiting device can not distinguish the genuine from the fake effectively, the first object of the present invention is to provide a tamperproof genuineness ID device with self-destruct protection function.

To overcome the shortcomings of current anti-counterfeiting method that it has no encryption protection means so that the counterfeiters can copy or fake it and then use the fake to imitate the true and that it is mainly depend on the similar extent with the anti-counterfeiting device by vision to identify the genuine or fake, the second object of the prevention invention is to provide a tamperproof genuineness ID method with self-destruct protection function.

To solve the above-mentioned first technical problem, the present invention provides a tamperproof genuineness ID device, comprising a working part with self-destruct protection function and a detecting work part for identifying a product to be detected, wherein the tamperproof genuineness ID device cooperates with the tamperproof genuineness ID device.

According to a preferred embodiment of the present invention, the tamperproof genuineness ID device and the product to be detected are integrated together by means of airtight sealing in a carrier via decompressing or pressurizing, or fixing to each other.

According to a preferred embodiment of the present invention, the working part with self-destruct protection function comprises a working part with pressure change self-destruct protection function or a working part with breakage self-destruct protection function, wherein the working part with pressure change self-destruct protection is triggered by pressure change in the sealed carrier.

According to a preferred embodiment of the present invention, the working part with self-destruct protection function comprises a working part with pressure change self-destruct protection function or a working part with breakage self-destruct protection function, wherein the working part with breakage self-destruct protection function is triggered by the change of relative position between the tamperproof genuineness ID device and the product to be detected.

According to a preferred embodiment of the present invention, the tamperproof genuineness ID device including the working part with self-destruct protection function is separated into a first working chamber and a second working chamber by a middle diaphragm which extends or shrinks in response to pressure change; wherein the first working chamber communicates with outside atmosphere, the second working chamber communicates with the carrier which accommodates the product to be detected and corporately retains an airtight sealed space with the carrier by decompressing or pressurizing; wherein the middle diaphragm is extended or shrunk by pressure changed in the second working chamber, so as to trigger the working part with pressure change self-destruct protection function.

According to a preferred embodiment of the present invention, the tamperproof genuineness ID device including the working part with breakage self-destruct protection function comprises magnetic substance which keeps a magnetic balance with the magnetic substance in the product to be detected, and the tamperproof genuineness ID device and the product to be detected are fixed together, wherein there is a magnetic switch disposed between the two magnetic substances, and the magnetic switch is controlled by the change of the magnetic balance to switch, so as to control the triggering of the working part with self-destruct protection function.

According to a preferred embodiment of the present invention, the tamperproof genuineness ID device further comprises a genuineness ID medium which cooperates with the detecting work part, wherein the genuineness ID medium stores random information therein, and all tamperproof genuineness ID code of the genuineness ID medium is hidden in the random information.

According to a preferred embodiment of the present invention, the tamperproof genuineness ID device comprises: a genuineness ID medium storing the random information therein, a microprocessor for reading, identifying, encrypting and calculating the tamperproof genuineness ID code in the genuineness ID medium; a self-destruct protection circuit to perform self-destruct protection for the microprocessor; a self-destruct trigger circuit for controlling the self-destruct protection circuit; a display device for displaying or broadcasting detecting result and a power source for supplying power to the above circuits and devices.

According to a preferred embodiment of the present invention, output terminals of the self-destruct trigger circuit are connected to a control signal input terminal of the self-destruct protection circuit, the self-destruct trigger circuit comprises at least one of a packaging breakage trigger circuit, a magnetic balance breaking trigger circuit, a photosensitive trigger circuit, a disassemble trigger circuit, an insufficient voltage trigger circuit, and a using tries limited trigger circuit; wherein the input terminal of the packaging breakage trigger circuit is connected with a packaging breakage trigger unit; the input terminal of the magnetic balance breaking trigger circuit is connected with a magnetic balance sensor; the input of the photosensitive trigger circuit is connected with a photo sensor; the input of the disassemble trigger circuit is connected with a disassemble trigger unit; the insufficient voltage trigger circuit has an input terminal connected to an output terminal of a power source; and the using tries limited trigger circuit has an input terminal connected to a using tries limited output terminal of the microprocessor.

According to a preferred embodiment of the present invention, the self-destruct protection circuit is a self-destruct voltage booster circuit or a stored/registered information deleted circuit.

The present invention also provides a tamperproof genuineness ID method with self-destruct protection function for detecting the tamper resistant tamperproof genuineness ID device via a genuineness ID medium, wherein the tamperproof genuineness ID device is airtight sealed or fixed with the product to be detected together, comprising the following steps: in the first step, setting the genuineness ID medium in a coordinate working state with the tamperproof genuineness ID device; in the second step, calculating information in the medium by the detecting work part of the device and getting a native genuineness ID code; and in the third step, outputting a detecting result.

According to a preferred embodiment of the present invention, the first step comprises the following sub-steps: in the first sub-step, determining whether the product to be detected and the tamperproof genuineness ID device are in an effective working state; in the second sub-step, setting the genuineness ID medium in a coordinate working state with the tamperproof genuineness ID device; and in the third sub-step, pressing an on-off button set on the tamperproof genuineness ID device to activate the tamperproof genuineness ID device.

According to a preferred embodiment of the present invention, the second step comprises the following sub-steps: in the first sub-step, reading, identifying and arranging a tamperproof genuineness ID code from the genuineness ID medium by the microprocessor of the tamperproof genuineness ID device which operates according to preset programs and instructions; in the second sub-step, performing encryption and calculation on the tamperproof genuineness ID code by the microprocessor which operates according to preset programs, instructions, and key, so as to get the native genuineness ID code; in the third sub-step, decoding the native genuineness ID code to get a converted native genuineness ID code; and in the four sub-step, determining whether the converted native genuineness ID code is identical with a preset native genuineness ID code which is unique to the genuineness ID medium.

According to a preferred embodiment of the present invention, the third step comprises display outputting or audio outputting.

Because the microprocessor of the tamperproof genuineness ID device with self-destruct protection function is equipped with self-destruct protecting circuits, the programs, instruction and encryption key set in the microprocessor are set in mask form during manufacturing of the microprocessor or written in after the self-destruct protection enabled and can't be read by exoteric device, illegal accessing the programs and encryption and performing encryption and calculation on them are efficiently prevented. Without obtaining the template, the tamperproof genuineness ID device, and the program and encryption key set therein cannot be copied and reproduced.

Compare with the conventional anti-counterfeiting means, the beneficial effects of the tamperproof genuineness ID method of the present invention are that because the present invention adopts a built-out randomly-coding genuineness ID card, the tamperproof genuineness ID code is hidden discretely in a long set of random information data and extracted there from via the programs and encryption key, and then is performed with multiple encryption and calculation to obtain a native genuineness ID code; and the hardware of the tamperproof genuineness ID device and software such as the programs and encryption key are protected by a self-destruction protection circuit; thus, the protected tamperproof genuineness ID method promotes the current "similar" or "not similar" identifying level to a level of "genuine" or "fake", which makes a genuineness ID detection for merchandise easier and more reliable.

BRIEF DESCRIPTION OF THE DRAWING

FIG. 1 is a circuit block diagram of a tamperproof genuineness ID device with self-destruct protection function in accordance with an embodiment of the present invention;

FIG. 2 is a cross sectional view of the tamperproof genuineness ID device with self-destruct protection function which arranged in carrier of the product to be detected;

DETAILED DESCRIPTION

Figure 3:
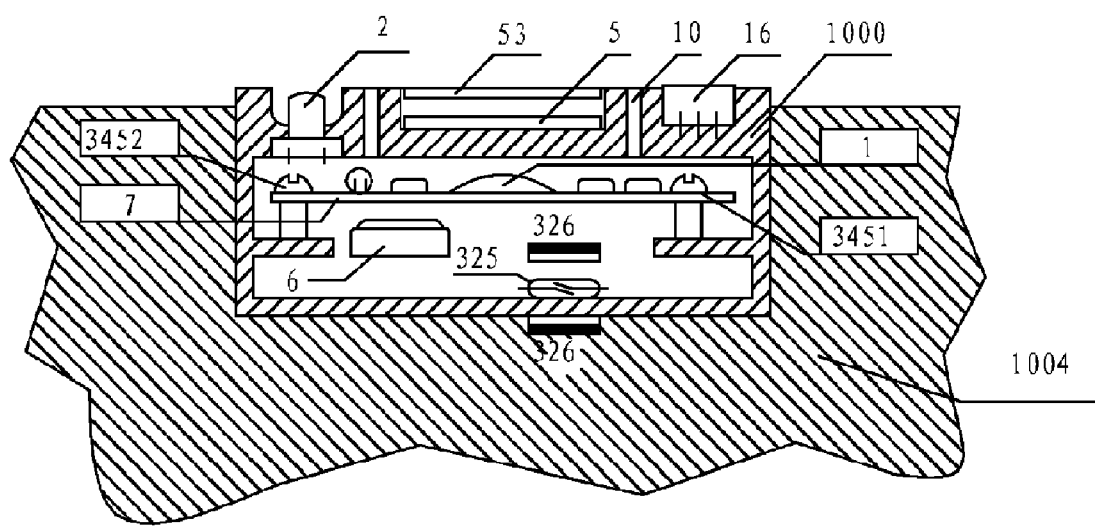
FIG. 3 is a cross sectional view of the tamperproof genuineness ID device with self-destruct protection function integrated with the product to be detected.

The present invention is described in the following embodiments with reference to the drawings.

The basic concept of the present invention is disclosed hereinafter. A variety of anti-counterfeiting means are presented on the market but get weak anti-counterfeiting effect. The root reason is that the chain of custody between the original-makers and the customer goes adrift. The anti-counterfeiting means, such as outer packaging made of special material and special structure, anti-counterfeiting marks, labels, and inquiry codes are not attached on the anti-counterfeiting merchandise itself. That is, these anti-counterfeiting means are presented before counterfeiters, and out of original-maker's control. The anti-counterfeiting means are not unique for original products, and are not anti-reproduce, anti-copy or anti-reuse after separated with the original product; so there are loopholes existing in logical concept. Accordingly, the counterfeiters can easily copy or reproduce the above anti-counterfeiting means, or even collect the used packaging of original products, and reuse them in the fake products. More seriously, there is no logical relationship between the anti-counterfeiting means and the merchandise to be identified; the true or fake of the anti-counterfeiting means and the true or fake of the merchandise constitute no necessary causality, therefore, violating categorical syllogism of logic. In this circumstance, even if an anti-counterfeiting means attached on a product is real, the product may still be a counterfeit, thereby leaving an insuperable barrier on logic function. The best solution is that every consumer purchases products directly from original manufactures. But for reality, it is almost impracticable. The solution disclosed in the present invention is to provide a tamperproof genuineness ID device with self-destruct protection function and a tamperproof genuineness ID method to distinguish the real from the fake. By this means, the chain of custody between the original-makers and customers is strengthened, and the chain of custody between the counterfeit and customers are broken; thereby achieving the same result as purchasing merchandise directly from the original-makers. The core of the present invention is that the tamperproof genuineness ID device and method for anti-counterfeiting of the present invention solve the technical problems of being unique for original product, being non-duplicable or non-reproducible, and being non-reusable after departing from original products. The true or fake of the tamperproof genuineness ID device and the true or fake of the merchandise constitute necessary causality, thereby achieving merchandise detection in practice.

The detailed working principle of the present invention is disclosed hereinafter. A tamperproof genuineness ID device is airtight sealed or fixed with the merchandise to be detected together. The tamperproof genuineness ID device and the product to be detected are airtight sealed together by decompressing or pressurizing, or they are fixed to each other, and a plurality of trigger circuits is used for triggering a self-destruct protection circuit, thereby preventing the tamperproof genuineness ID device from being copied or reused, and preventing programs, instructions and encryption keys stored in a microprocessor from being stolen. During the implementing of the present invention, genuineness ID medium is provided to customers and supervisions by professional institute having public credibility. In this embodiment, the genuineness ID medium is a tamperproof genuineness ID card. In other embodiments, the genuineness ID medium can also adopts other carriers, such as a cell phone. The card cooperates with the tamperproof genuineness ID device to distinguish the genuine from the fake. To prevent information stored in the card from being illegally accessed, there is a set of binary random information data with enough length stored in the card. Tamperproof genuineness ID code occupies only a small part of the binary random information data, and is discretely distributed in the information data. The tamperproof genuineness ID code may not be the native genuineness ID code. Accordingly, even if all of the binary random information data in the card are accessed, the tamperproof genuineness ID code cannot be extracted from the information data, and the native genuineness ID code cannot be got from the tamperproof genuineness ID code further. The tamperproof genuineness ID code can only be identified by the programs stored in the microprocessor of the tamperproof genuineness ID device. The native genuineness ID code is unique for each card, and can be got only by performing multiple encryptions and calculations on the tamperproof genuineness ID code and the encryption key. The native genuineness ID code after decryption is displayed on the tamperproof genuineness ID device or sounded by the tamperproof genuineness ID device. The customer can compare the native genuineness ID code after decryption with a code which has already stored in his card, to identify whether the product to be detected is true. Thus, the identifying result is very accurate. Only the device which can encrypt the unique native genuineness ID code of the card is the true tamperproof genuineness ID device, and the true product is the one which is inseparable with the real tamperproof genuineness ID device.

Referring to FIG. 1, a circuit block diagram of the tamperproof genuineness ID device with self-destruct protection function is illustrated. Referring to FIG. 2, a cross-sectional view of the tamperproof genuineness ID device with self-destruct protection function which arranged in carrier of the product to be detected is illustrated, and FIG. 3, a cross-sectional view illustrates the tamperproof genuineness ID device with self-destruct protection function integrated with the original self-destruct merchandise.

As shown in the figures, a tamperproof genuineness ID device with self-destruct protection function 1000 in accordance with a preferred embodiment of the present invention includes a working part with self-destruct protection function and a detecting work part identifying a product to be detected, and the tamperproof genuineness ID device 1000 cooperates with the product to be detected 1004. In this embodiment, the working part with self-destruct protection function adopts a self-destruct protection circuit 4, and it is obvious that the working part with self-destruct protection function can adopt other self-destruct protection circuits. The tamperproof genuineness ID device 1000 and the product to be detected 1004 are integrated together by means of airtight sealing in a carrier 1003 via decompressing or pressurizing, or fixing to each other. The working part with self-destruct protection function can be a working part with pressure change self-destruct protection function or a working part with breakage self-destruct protection function. The working part with pressure change self-destruct protection function is triggered by the change of pressure in the sealed carrier 1003; and the working part with breakage self-destruct protection function is triggered by the change of relative position change between the tamperproof genuineness ID device 1000 and the original product to be detected 1004.

In particular, the tamperproof genuineness ID device 1000 with self-destruct protection function includes a built-out tamperproof genuineness ID card 8 and a main body 1000. The main body 1000 of the tamperproof genuineness ID device includes a microprocessor 1, a self-destruct protection circuit 4 connected to the microprocessor 1, a self-destruct trigger circuit 3 for controlling the self-destruct protection circuit 4, a display device 5 for displaying detecting result or an audio device for broadcasting detecting result, and a power source 6 for supplying power to the above circuits and devices.

In this embodiment, the microprocessor 1 is an ultra-micro power digital microprocessor chip. An output terminal 14 of the microprocessor 1 is connected to an input terminal 52 of the display device 5. On-off control terminals 11, 12 of the microprocessor 1 are connected with an on-off button 2. An identifying input terminal of the microprocessor 1 is connected with a card slot 16 for insertion of the tamperproof genuineness ID card 8. An output plug 81 of the built-out tamperproof genuineness ID card 8 can be inserted in the card slot 16 of input terminal of the microprocessor 1. In other embodiments, the tamperproof genuineness ID card 8 and the tamperproof genuineness ID device 1000 can cooperate via no-inserted means, such as radio frequency. The self-destruct protection circuit can be a chipset self-destruct voltage booster circuit 4 or stored/registered information deleted circuit, in this embodiment, it is the former. The self-destruct trigger circuit 3 comprises a packaging breakage trigger circuit 31, a magnetic balance breaking trigger circuit 32, a photosensitive trigger circuit 33, a disassemble trigger circuit 34, an insufficient voltage trigger circuit 35, and a using tries limited trigger circuit 36. The using tries limited trigger circuit 36 is connected to a using tries limited output terminal 17 of the microprocessor 1, and is controlled for tries limited use by the microprocessor 1. A high-voltage output terminal 42 of the chipset self-destruct voltage booster circuit is connected to a self-destruct input terminal 15 of the microprocessor 1. Output terminals 312, 322, 332, 342, 352, and 362 of the packaging breakage trigger circuit 31, the magnetic balance breaking trigger circuit 32, the photosensitive trigger circuit 33, the disassemble trigger circuit 34, the insufficient voltage trigger circuit 35, and the using tries limited trigger circuit 36 are all connected to a control signal input terminal 43 of the chipset self-destruct voltage booster circuit 4. The packaging breakage trigger circuit 31 of the self-destruct voltage booster circuit includes a trigger switch 315 which is triggered in response of pressure change in packaging or carrier 1003 of the product to be detected. The magnetic balance breaking trigger circuit 32 includes a magnetic balance sensor which comprises magnetic substance 326 and a magnetic switch 325. The photosensitive trigger circuit 33 includes a photo sensor 335. The disassemble trigger circuit 34 includes an anti-disassemble switch 345. Power input terminals 311, 321, 331, 341, 351, 361 of the trigger circuits 31, 32, 33, 34, 35, 36, and power input terminals 41, 13, 51 of the chipset self-destruct voltage booster circuit 4, the microprocessor 1, and the display device 5 are all connected to a power output terminal 61 of the battery 6.

Referring to FIGS. 2 and 1, the tamperproof genuineness ID device 1000 is separated into a first working chamber 1001 and a second working chamber 1002 by a sealing diaphragm 316. The diaphragm 316 extends or shrinks in response to pressure difference between two sides. The second working chamber 1002 communicates with the carrier 1003 which accommodating the product to be detected 1004 and is airtight sealed together with the carrier 1003. The second working chamber 1002 and the carrier 1003 corporately retain an airtight sealed space. The deformation of the diaphragm 316 caused by pressure change in the second working chamber 1002 triggers the self-destruct protection circuit 4, thereby protecting the programs, instructions and encryption key of the microprocessor 1 of the tamperproof genuineness ID device 1000 from being accessed illegally.

In this embodiment, the display device 5 is attached to an inner surface of the carrier 1003, facing outside. The carrier 1003 is a packaging bag or box. The display device 5 is covered with a transparent protection sheet 53. The main body of the tamperproof genuineness ID device 1000 is separated into two working chambers by the sealing diaphragm 316. The chamber above the sealing diaphragm 316 is defined as the first working chamber 1001 which communicates with the outside atmosphere through vents 10 on a panel of main body of the tamperproof genuineness ID device 1000. Therefore, the pressure in the first working chamber 1001 equals to the atmospheric pressure. The chamber under the sealing diaphragm 316 is defined as the second working chamber 1002 which communicates with the carrier 1003 through vents 11 defined in a bottom of the tamperproof genuineness ID device 1000. The diaphragm 316 either has positive pressure or has negative pressure on one side thereof by decompressing or pressurizing in the second working chamber 1002 and the carrier 1003. The pressure difference between the second working chamber 1002 and the outside atmosphere is great enough to extend or shrink the diaphragm 316. When the second working chamber 1002 and the carrier 1003 are vacuumed, or the carrier 1003 is vacuumed, the diaphragm 316 shrinks down to release the trigger switch 315. For instance, in the state of releasing the trigger switch 315, the packaging breakage trigger circuit 31 is set as a standby state. If the tamperproof genuineness ID device 1000 is departed from the original product to be detected, once the carrier 1003 is broken, the outside air will enter the second working chamber 1002 immediately. There is no pressure difference between the second working chamber 1002 and the outside atmosphere, and the diaphragm 316 returns to its original position from the shrunk state to press against the trigger switch 315. As a result, the packaging breakage trigger circuit 31 is triggered, and sends a control signal to the self-destruct protection circuit 4. The self-destruct protection circuit 4 outputs a high voltage to destroy the programs, instructions, and encryption key of the microprocessor 1. In other embodiments, the second chamber 1002 and the carrier 1003, or the carrier 1003 can be pressurized, and the diaphragm 316 extends up to press against the trigger switch 315. For instance, in the state of pressing against the trigger switch 315, the packaging breakage trigger circuit 31 is set as a standby state. If the tamperproof genuineness ID device 1000 is departed from the original product to be detected, once the carrier 1003 is broken, the inner air is expelled from the second chamber 1002. There is no pressure difference between the second working chamber 1002 and the outside atmosphere, and the diaphragm 316 returns to its original position from the extended state to release the trigger switch 315. As a result, the packaging breakage trigger circuit 31 is triggered, and sends a control signal to the self-destruct protection circuit 4. The self-destruct protection circuit 4 outputs a high voltage to destroy the programs, instructions, and encryption key of the microprocessor 1.

Referring to FIGS. 3 and 1, the tamperproof genuineness ID device 1000 with a working part with self-destruct protection function includes a magnetic substance 326 therein. The magnetic substance 326 in the tamperproof genuineness ID device 1000 is in magnetic balance with a magnetic substance 326 on the original product to be detected 1004. The original product to be detected 1004 and the tamperproof genuineness ID device 1000 are fixed to each other. The magnetic switch 325 is disposed between the two magnetic substances 326. If the relative position between the tamperproof genuineness ID device 1000 and the product to be detected 1004 is changed, the magnetic balance is broken, and the magnetic switch 325 triggers the working part with breakage self-destruct protection function. In this embodiment, the magnetic substance 326 in the tamperproof genuineness ID device 1000 and the magnetic substance 326 in the original product to be detected 1004 have the same magnetic density and have the same polarities facing each other. The magnetic switch 325 is disposed at the middle position of the balance magnetic field between the two magnetic substances 326. The two magnetic substances 326 and the magnetic switch 325 form the magnetic balance sensor. The magnetic switch 325 is a reed pipe. Thus, the relative position change of the tamperproof genuineness ID device 1000 and the original product to be detected 1004 triggers the self-destruct protection for the programs, instructions and encryption key of the microprocessor 1 of the tamperproof genuineness ID device 1000.

In addition, in this embodiment, when the tamperproof genuineness ID device 1000 is disassembled, the photo sensor 335 of photosensitive trigger circuit 33 receives light, and the resistance of the photo sensor 335 is become very low from extreme high, thereby triggering the photosensitive trigger circuit 33. The disassemble trigger circuit 35 comprises series connected anti-disassemble contact points 3451 and fasteners 3452, wherein the anti-disassemble contact points 3451 are arranged in the position pressed by the fasteners 3452 on a circuit board 7, and electric connected by the metal end of the fasteners 3452. If any one of the fasteners 3452 for fixing the circuit board 7 is loosened, the series connected switch 345 will change to open state from closed state and triggers the disassemble trigger circuit 34. The insufficient voltage trigger circuit 35 is a voltage comparison circuit. If the voltage of the battery 6 in the tamperproof genuineness ID device 1000 drops to a predetermined level, the insufficient voltage trigger circuit 35 is triggered. The working principle of the using tries limited trigger circuit 36 is that, after the microprocessor 1 has been used for predetermined times, the using tries limited output terminal 17 of the microprocessor 1 outputs a trigger signal to an input terminal 363 of the using tries limited trigger circuit 36 to trigger the using tries limited trigger circuit 36. Once at least one of the above described trigger circuits is triggered, the high-voltage output terminal 42 of the self-destruct protection circuit 4 outputs a high voltage to the self-destruct input terminal 15 of the microprocessor 1 to cause breakdown of the microprocessor 1 and destroy the programs, instructions and encryption key of the microprocessor 1, and cause permanent disenablement of the tamperproof genuineness ID device 1000.

In order not to destroy the microprocessor 1 during the process of assembling and testing the tamperproof genuineness ID device 1000, an insulation soft strip (not shown) is disposed to the power input terminal 41 or the high-voltage output terminal 42 of the self-destruct protection circuit 4. When the assembly and testing of the tamperproof genuineness ID device 1000 is finished, the startup time is clear as "0", and the second working chamber 1002 and the carrier 1003 is increased or decreased. Then, the insulation soft strip is taken out through the panel of the tamperproof genuineness ID device 1000 and the self-destruct voltage booster circuit 4 is switched on. The insulation soft strip is made of very thin and flexible insulated material, thus cannot be placed back to the assembled tamperproof genuineness ID device 1000.

Figure 4:
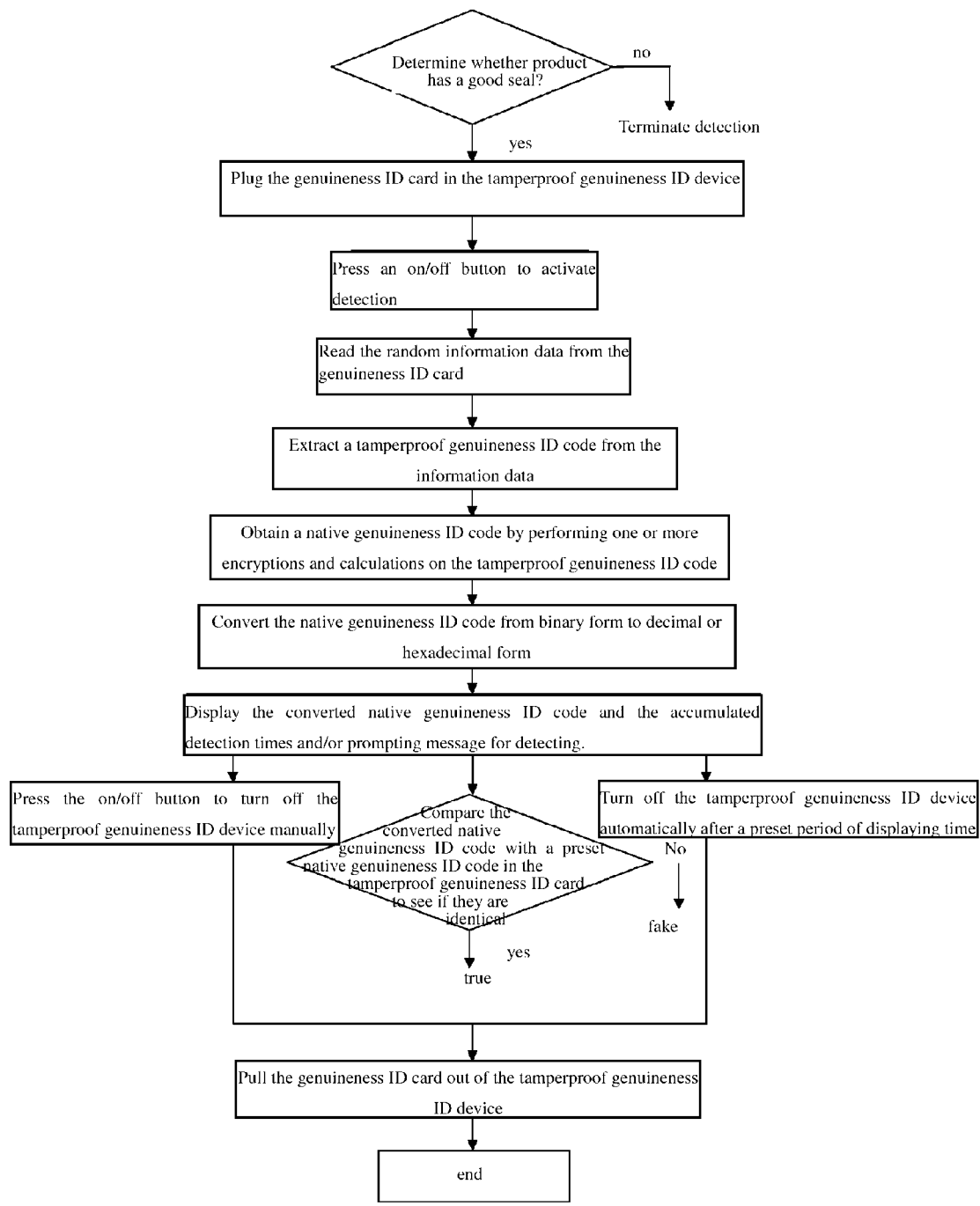
FIG. 4 is a flow chart of a tamperproof genuineness ID method using the tamperproof genuineness ID device with self-destruct protection function in accordance with an embodiment of the present invention.

Referring to FIG. 4, a detecting process in accordance with a preferred embodiment of the present invention is illustrated. Firstly, determine whether the product to be detected has a good seal. If no, terminate detection. If yes, the genuineness ID card 8 is inserted into the card slot 16 of the tamperproof genuineness ID device 1000. If a radio frequency identifying card is used, just place the card near the tamperproof genuineness ID device 1000. Push the on-off button 2 to determine whether the tamperproof genuineness ID device 1000 is activated, that is, whether the product to be detected is under effective protection of the tamperproof genuineness ID device 1000. If the tamperproof genuineness ID device 1000 cannot be activated, it means the tamperproof genuineness ID device 1000 has been self-destruct and the detection can not be performed. If the product to be detected is under effective protection of the tamperproof genuineness ID device, go to the following steps. Firstly, identify the tamperproof genuineness ID code. The tamperproof genuineness ID device 1000 reads the information data in the detecting card 8 according to preset programs and instructions, and extracts and arranges the tamperproof genuineness ID code hidden discretely therein. Then, perform multiple encryptions and calculations to the tamperproof genuineness ID code with the encryption key. That is, the tamperproof genuineness ID device 1000 performs calculation on the tamperproof genuineness ID code according to preset programs and instructions, so as to get the complement code, reverse code, inverse code and offset code of the tamperproof genuineness ID code. Then at least one of the above codes is selected according to randomly set programs and instructions, and is combined with the encryption key in the microprocessor 1 of the tamperproof genuineness ID device 1000. Then perform single step encryption and calculation or multi-step encryption and calculation, including full-adding (with carry), half-adding (without carry), mix-adding, minus, multiply, and division to get the native genuineness ID code which is substantially different from genuineness ID information. However, the native genuineness ID code is not the tamperproof genuineness ID code for identifying by the user. The microprocessor 1 of the tamperproof genuineness ID device 1000 further decodes the native genuineness ID code of binary form into decimal or hexadecimal form to get the native genuineness ID code which can be displayed or broadcasted. The decoded native genuineness ID code is sent to the display device 5 of the tamperproof genuineness ID device 1000 to display or to an audio circuit to broadcast by the microprocessor 1 of the tamperproof genuineness ID device 1000. Prompting messages are synchronously displayed, or the prompting voice is synchronously sounded. Accumulated times for which the tamperproof genuineness ID device 1000 has been used are also displayed. Users compare the displayed or broadcasted information with the native genuineness ID code which is unique for and preset in the genuineness ID card 8, and determine whether the product to be detected is true or counterfeit. After testing, the users can turn off the push button 2 on the panel of the tamperproof genuineness ID device 1000, and pull out the genuineness ID card 8 from the tamperproof genuineness ID device 1000.

The detailed identifying and encryption processes of the information data in the genuineness ID card 8 of the tamperproof genuineness ID device 1000 are illustrated as the following embodiment.

The tamperproof genuineness ID code of the genuineness ID card 8 is a table of randomly arranged binary code. For example, the tamperproof genuineness ID code in the following table is arranged in a great deal information data in groups each having four bits.

| Card I | Information data stored in the card (only the tamperproof genuineness ID code is listed) | . . . 1001 . . . 0011 . . . 1110 . . . 1010 . . . 0101 . . . 1010 |
|---|---|---|
| Card II | Information data stored in the card (only the tamperproof genuineness ID code is listed) | . . . 0010 . . . 1011 . . . 0111 . . . 0010 . . . 0100 . . . 0011 |

The tamperproof genuineness ID code is extracted from the information data and arranged according to address by the programs and instructions set in the microprocessor 1. In this embodiment, the tamperproof genuineness ID code is arranged into six groups, stored in addresses 1050, 3680, 15606, 23168, 57860, and 153686 of the card 8, respectively.

| Card I | Identified and arranged tamperproof genuineness ID codes | 1001 0011 1110 1010 0101 1101 |
|---|---|---|
| Card II | Identified and arranged tamperproof genuineness ID codes | 0010 1011 0111 0010 0100 0011 |

After the microprocessor 1 gets the tamperproof genuineness ID code, the microprocessor 1 calculates to get the complement code of the tamperproof genuineness ID code, and performs full add to the complement code and the encryption key registered in the microprocessor 1, to obtain the native genuineness ID code as follows.

| Card I | encryption key set in the microprocessor | 1000 1111 0001 0011 0110 1100 |
|---|---|---|
| | complement code | 0110 1100 0001 0101 1010 0011 |
| | Native genuineness ID code | 1111 1011 0010 1001 0000 1111 |
| Card II | encryption key set in the microprocessor | 1000 1111 0001 0011 0110 1100 |
| | complement code | 1101 0100 1000 1101 1011 1101 |
| | Native genuineness ID code | 0110 0011 1010 0001 0010 1001 |

Decode the native genuineness ID code from binary form to hexadecimal form to get the native genuineness ID code. In this embodiment, besides the ten Arabic numbers 0-9, the weights of H, L, P, C, F, and E are set as 10, 11, 12, 13, 14, and 15 in the hexadecimal system.

| Card I | tamperproof genuineness ID code | EL290E |
|---|---|---|
| Card II | tamperproof genuineness ID code | 63H129 |

Of course, the means of identifying, arranging, encrypting, calculating and decoding may be various, and are not limited to the above embodiment.

A large network of product to be detected can be established by the anti-counterfeiting technique of the present invention. Two aspects must be concerned during the checking. First, special authoritative institution distributes the genuineness ID card 8. Second, accept manufactures of brand product to be detected into the network. The tamperproof genuineness ID devices are supplied to the manufactures of brand product to be detected by designated manufactures of the tamperproof genuineness ID devices. The manufactures of brand product to be detected vacuumize or pressurize the carrier 1003, and seal the tamperproof genuineness ID device 1000 into the carrier 1003 accommodating the product to be checked, so that the tamperproof genuineness ID device 1000 and the product to be checked are airtight sealed or fixed together before sale. Preferably, the cards 8 are distributed as more as possible and the manufactures of brand product to be detected as more as possible participate in, to enlarge the anti-counterfeiting network using the technique of the present invention. The anti-counterfeiting network using the accurate and effective technique is enlarged gradually, the fake product will disappear in the scope of the network, and the protection of brand product and customers is improved furthest.

The function and result of the tamperproof genuineness ID device of the present invention are disclosed in detail as follows:

First, the microprocessor 1 of the tamperproof genuineness ID device 1000 is equipped with a self-destruct protection circuit. As a result, the tamperproof genuineness ID device 1000 can only perform detection upon a condition that the product to be detected packaging keeps its integrity. Two measures are used to ensure the tamperproof genuineness ID device 1000 is unique for its attached true product. The first measure is that the detecting programs and encryption key are set in mask form during manufacturing the microprocessor or written in after the self-destruct protection function is enabled, and can't be read by exoteric device. The programs and encryption key are kept secret during assembly, test, and use of the tamperproof genuineness ID device 1000. The second measure is that after the tamperproof genuineness ID device 1000 and the original product to be detected 1004 are airtight sealed together by vacuumizing or pressurizing, once the packaging is broken or even a tiny pinhole occurs, the low or high pressure inside the second working chamber 1002 of the checking device 1000 and the package will disappear immediately. The packaging breakage trigger circuit 31 triggers the self-destruct protection circuit 4 to output a high voltage to the self-destruct input terminal 15 to destroy the programs, instructions and encryption keys in the microprocessor 1. The tamperproof genuineness ID device 1000 including the working part with breakage self-destruct protection function comprises magnetic substance 326 which keeps a magnetic balance with the magnetic substance 326 in the product to be detected 1004, and the tamperproof genuineness ID device 1000 and the product to be detected 1004 are fixed together, wherein there is a magnetic switch 325 disposed between the two magnetic substances 326. Because the magnetic switch 325 is in magnetic balance when the tamperproof genuineness ID device 1000 and the product to be detected 1004 are fixed together, once the tamperproof genuineness ID device 1000 is moved relative to the product to be detected 1004, the magnetic balance is broken, the magnetic switch 325 is turned on to trigger the working part with breakage self-destruct protection function. A high voltage is sent to the self-destruct input terminal 15 of the microprocessor 15 to destroy the programs, instructions, and encryption keys in the microprocessor 1. Thus, only when the original product to be detected is equipped with a tamperproof genuineness ID device that is not destructed, the tamperproof genuineness ID code can be encrypted later on. Therefore, the tamperproof genuineness ID device is exclusive for the original product to be detected.

Second, the tamperproof genuineness ID device is not replicable or counterfeitable. Reproducing needs template. However, although all the hardware can be reproduced according to the disclosed principle and function, the programs, instructions, and encryption key set in the microprocessor 1 cannot be copied or read illegally. When one of below circumstances occurs, i.e., the carrier or packaging 1003 of the original product to be detected 1004 leaks air, the separation of the tamperproof genuineness ID device 1000 and the original product to be detected 1004, the tamperproof genuineness ID device 1000 is broken to have inner part receives light, the fasteners 3452 are loosened from the circuit board 7, the power source 6 is exhausted, or the detecting times reaches the predetermined limit set in the microprocessor 1, the self-destruct protection circuit 4 is triggered to generate a high voltage to destroy the programs, instructions, and encryption key in the microprocessor 1 immediately. Thus, the programs which can not be read illegally and the self-destruct protection circuit provides complete protection for the tamperproof genuineness ID device 1000, so that the tamperproof genuineness ID device 1000 is not reproducible, and the counterfeiter cannot obtain any template from the tamperproof genuineness ID device 1000.

Third, the tamperproof genuineness ID device 1000 cannot be reused after being disassembled from the original product to be detected. As mentioned above, the programs, instructions, and encryption key set in the microprocessor 1 is destroyed immediately and disenable the tamperproof genuineness ID device after the tamperproof genuineness ID device 1000 leaves the original product to be detected.

Fourthly, the genuineness ID card 8 has special functions. Because the random information data stored in the card 8 needs to be accessed during use, illegal access is hard to be avoided. Therefore, there is a need to preventing extracting and arranging the tamperproof genuineness ID codes from a set of random information data after the card 8 is accessed illegally. Solutions are taken in the present invention to solve the problem. Firstly, the tamperproof genuineness ID code only occupies a small part of the set of information data, and is discretely hidden in the information data. Even if the counterfeiter accesses all of the information data, he still cannot extract the useful tamperproof genuineness ID codes for the lack of programs indicating addresses and orders of the tamperproof genuineness ID codes. Secondly, the set of information data is randomly organized in binary form. Even the encoding person does not know how information data is coded in the next card. After the genuineness ID card 8 is written with the mass random information data, the encoding person will utilize a card reader which has the same programs and encryption key as the microprocessor to read the tamperproof genuineness ID codes from the information dada, and then the tamperproof genuineness ID codes are printed or sealed on the genuineness ID card 8. The card 8 is given to a user and as the only tool to determine whether the product is true or fake. Therefore, the counterfeiter is unable to track the coding process. Thirdly, when the genuineness ID card 8 is plugged into the tamperproof genuineness ID device 1000, only the tamperproof genuineness ID device 100 can extract the tamperproof genuineness ID codes from the information data rapidly according to the programs set in the tamperproof genuineness ID device 1000. Fourthly, the tamperproof genuineness ID code can be or can be not the native genuineness ID code. If the tamperproof genuineness ID code is not the native genuineness ID code, the tamperproof genuineness ID device 1000 performs calculation on the tamperproof genuineness ID code according to preset programs and instructions, so as to get the complement code, reverse code, inverse code and offset code of the tamperproof genuineness ID code. Then at least one of the above codes is selected according to randomly set programs and instructions, and is combined with the encryption key in the microprocessor 1 of the tamperproof genuineness ID device 1000. Then perform single step encryption and calculation or multi-step encryption and calculation, including full-adding (with carry), half-adding (without carry), mix-adding, minus, multiply, and division to get the native genuineness ID code which is substantially different from genuineness ID information. The microprocessor 1 of the tamperproof genuineness ID device 1000 further decodes the native genuineness ID code of binary form into decimal or hexadecimal form to get the native genuineness ID code which can be displayed on the display device of the checking device for comparison. The native genuineness ID code is substantially different from genuineness ID information. The checking device 1000 can get the native genuineness ID code only by identifying, arranging, and weighting the information data in the card 8 according to preset programs and instructions. Thus, even the counterfeiters get the original information data in the card 8, they can not know the programs, instructions and encrypting key by which the checking device 1000 identifying, arranging, and weighting the information data in the card 8.

Fifthly, the counterfeiter will not copy or reproduce the genuineness ID card 8. The counterfeiter will not just reproduce the genuineness ID card and its exact information data, because it is only making card for the original product but cannot identify a fake product as an original one. If the counterfeiter writes a set of new information data in a fake card, the tamperproof genuineness ID device 1000 cannot obtain a native genuineness ID code through extracting and encrypting from the fake card. In addition, the counterfeiter cannot track and obtain the tamperproof genuineness ID code unique for each card. Furthermore, the fake card cannot enter formal distribution channel, because it is not distributed by the special institute and no one will accept it.

Sixthly, in order to prolong the detecting function of the present invention, the native genuineness ID code can be upgraded at any time. When upgraded, the programs, instructions and encrypting key in the processor of the checking device is modified and the bit of the tamperproof genuineness ID code is increased or decreased, without any change of the checking card. User can upgrade his card via the distributing institute or via the upgraded product to be detected. The person can write down the updated native genuineness ID code which is unique for his own card to update. In the transition time, the old version tamperproof genuineness ID device and the upgraded tamperproof genuineness ID device can be used both.

The tamperproof genuineness ID device and method with self-destruct protection function can be applied in very broad field. It can identify product to be detected in logistics, and prevent product to be detected in transport from being exchanged. The tamperproof genuineness ID device utilizes an ultra-micro power digital microprocessor 1 whose standby current is only several nano-amperes. Lifespan of the battery can last for several years. As the development of the technology, microprocessor of lower consumption and battery of greater capability may be used to prolong the life of the checking device 1000. In addition, when the battery is going to be exhausted, the insufficient voltage trigger circuit 35 will trigger the self-destruct protection circuit 4 to output a high voltage to damage the programs and encryption key of the microprocessor 1, thereby preventing the tamperproof genuineness ID device 1000 from being accessed when the battery 6 are exhausted.

In this embodiment, the diaphragm 316 is a sheet of flexible rubber material anchored at its periphery and spherical in shape. The diaphragm 316 can also be other shape and structure that can be deformed by pressure change at its two opposite sides and restored when the pressure change disappears. To ensure the self-destruct protection function, besides the packaging breakage trigger circuit 31 and the magnetic balance breaking trigger circuit 32 which are necessary, one or more of the other trigger circuits such as photosensitive trigger circuit 33, disassemble trigger circuit 34, insufficient voltage trigger circuit 35, and using tries limited trigger circuit 36 can also be applied. For some special product to be detected or special customer requirements, the detecting result can be indicated by sound instead of by display. For example, a sounding device can be applied to read out the converted native genuineness ID code, and the display device is changed to a low power consumption amplifier and a micropower electro acoustic device. In other embodiment, the on-off bottom can be omitted, and replaced by a contact switch installed in the card slot 16 of the tamperproof genuineness ID device 1000. When the genuineness ID card 8 is plugged in the card slot 16, the contact switch is triggered and activates the tamperproof genuineness ID device 1000. When the genuineness ID card 8 is pulled out of the card slot 16, the tamperproof genuineness ID device 1000 is turned off automatically. The pressure in the first working chamber 1001 can not the atmospheric pressure, as long as it makes sure that when the pressure in the second chamber 1002 changes, the sealing diaphragm extents or shrinks to trigger the packaging breakage trigger circuit 31.

In this embodiment, another display device can be installed on the genuineness ID card 8. Therefore, the detecting result can be displayed respectively on the checking device 1000 and the card 8, or be displayed on the both simultaneously.

The disclosure is illustrative only, and one skilled in the art can obtain various embodiments according to different requirements without departing the scope and spirit of the present invention.

What is claimed is:

1. A tamperproof genuineness ID device with self-destruct protection function, wherein the tamperproof genuineness ID device comprising a working part with self-destruct protection function and an detecting work part for processing data;

wherein the tamperproof genuineness ID device and a product to be detected are airtight sealed or fixed together, and the a working part with self-destruct protection function are arranged in the airtight sealed or fixed state of the tamperproof genuineness ID device and the product to be detected; and the detecting work part comprises a data input interface, the detecting work part reads information data from an out-built tamper-resistant medium via the data input interface wherein, the built-out tamper-resistant medium is a tamper-resistant card, the tamper-resistant card is stored with random information data, and a tamperproof genuineness ID code unique for the tamper-resistant medium is hidden in the random information data;

the tamperproof genuineness ID device and the product to be detected are integrated together by means of sealing in a carrier via decompressing or pressurizing;

the working part with self-destruct protection function comprises a working part with pressure change self-destruct protection function or a working part with breakage self-destruct protection function, wherein the working part with pressure change self-destruct protection is triggered by pressure change in the sealed carrier;

the tamperproof genuineness ID device including the working part with pressure change self-destruct protection function is separated into a first working chamber and a second working chamber by a middle diaphragm which extends or shrinks in response to pressure change;

wherein the first working chamber communicates with outside atmosphere, the second working chamber communicates with a carrier which accommodates the product to be detected; wherein the middle diaphragm is extended or shrunk by pressure changed in the second working chamber, so as to trigger the working part with pressure change self-destruct protection function.

2. The tamperproof genuineness ID device as claimed in claim 1, wherein the detecting work part comprises a device for displaying or broadcasting a detecting result.

3. The tamperproof genuineness ID device as claimed in claim 1, wherein the working part with breakage self-destruct protection function is triggered by the change of relative position between the tamperproof genuineness ID device and the product to be detected.

4. The tamperproof genuineness ID device as claimed in claim 3, wherein the tamperproof genuineness ID device including the working part with breakage self-destruct protection function comprises magnetic substance which keeps a magnetic balance with the magnetic substance in the product to be detected, and the tamperproof genuineness ID device and the product to be detected are fixed together, wherein there is a magnetic switch disposed between the two magnetic substances, and the magnetic switch is controlled by the change of the magnetic balance to switch, so as to control the triggering of the working part with breakage self-destruct protection function.

5. The tamperproof genuineness ID device as claimed in claim 1, wherein the detecting work part comprises:

a microprocessor for reading, identifying, and encrypting a tamperproof genuineness ID code of the tamper-resistant medium according to preset rule;

the working part with self-destruct protection function comprises:

a self-destruct protection circuit to perform self-destruct protection for the microprocessor; and a self-destruct trigger circuit for controlling the self-destruct protection circuit; and the tamperproof genuineness ID device further comprises:

a power source for supplying power to the above circuits.

6. The tamperproof genuineness ID device as claimed in claim 5, wherein output terminals of the self-destruct trigger circuit are connected to a control signal input terminal of the self-destruct protection circuit, the self-destruct trigger circuit comprises at least one of a packaging breakage trigger circuit, a magnetic balance breaking trigger circuit, a photosensitive trigger circuit, a disassemble trigger circuit, an insufficient voltage trigger circuit, and a using tries limited trigger circuit;

wherein the input terminal of the packaging breakage trigger circuit is connected with a packaging breakage trigger unit;

the input terminal of the magnetic balance breaking trigger circuit is connected with a magnetic balance sensor;

the input of the photosensitive trigger circuit is connected with a photosensor;

the input of the disassemble trigger circuit is connected with an disassemble trigger unit;

the insufficient voltage trigger circuit has an input terminal connected to a output terminal of a power source; and the using tries limited trigger circuit has an input terminal connected to a using tries limited output terminal of the microprocessor.

7. The tamperproof genuineness ID device as claimed in claim 5, wherein the self-destruct protection circuit is a self-destruct voltage booster circuit or a stored/registered information deleted circuit.

8. A tamperproof genuineness ID method with self-destruct function by employing the tamperproof genuineness ID device with self-destruct protection function according to claim 1, wherein, the tamperproof genuineness ID method comprises the steps of:

A. setting the tamper-resistant medium in a coordinate working state with the tamperproof genuineness ID device;

B. identifying and alining the tamperproof genuineness ID code from random information code in the tamper-resistant medium by the detecting work part of the tamperproof genuineness ID device which operates according to preset programs and instructions, and performing encryption and calculation to the tamperproof genuineness ID code to get the native genuineness ID code; and C. outputting a detecting result.

9. The tamperproof genuineness ID method as claimed in claim 8, wherein the step A comprises the steps of:

A1. determining whether the product to be detected and the tamperproof genuineness ID device are in an effective working state;

A2. setting the tamper-resistant medium in a coordinate working state with the tamperproof genuineness ID device; and A3. pressing an on-off button set on the tamperproof genuineness ID device to activate the tamperproof genuineness ID device.

10. The tamperproof genuineness ID method as claimed in claim 9, wherein the step B comprises the steps of:

B1. reading, identifying and arranging a tamperproof genuineness ID code from the tamper-resistant medium by the microprocessor of the tamperproof genuineness ID device which operates according to preset programs and instructions;

B2. performing encryption and calculation on the tamperproof genuineness ID code by the microprocessor which operates according to preset programs, instructions and encrypting key, so as to get the native genuineness ID code;

B3. decoding the native genuineness ID code to get a converted native genuineness ID code and displaying on a display device; and B4. determining whether the converted native genuineness ID code is identical with a preset native genuineness ID code which is unique to the tamper-resistant medium.

11. The tamperproof genuineness ID method as claimed in claim 8, wherein the step C comprises display outputting and/or audio outputting.

* * * * *